United States Patent
Hoenes et al.

(10) Patent No.: US 9,604,208 B2
(45) Date of Patent: Mar. 28, 2017

(54) TEST DEVICE FOR ANALYZING BODY FLUIDS

(75) Inventors: Joachim Hoenes, Zwingenberg (DE); Hans List, Hesseneck-Kailbach (DE); Karl Miltner, Frankenthal (DE); Wilfried Schmid, Mannheim (DE)

(73) Assignee: Roche Diabetes Care, Inc., Indinanapolis, IN (US)

( * ) Notice: Subject to any disclaimer, the term of this patent is extended or adjusted under 35 U.S.C. 154(b) by 2846 days.

(21) Appl. No.: 11/384,951

(22) Filed: Mar. 20, 2006

(65) Prior Publication Data

US 2006/0216817 A1  Sep. 28, 2006

Related U.S. Application Data

(63) Continuation of application No. PCT/EP2004/010289, filed on Sep. 15, 2004.

(30) Foreign Application Priority Data

Sep. 19, 2003 (DE) .................................. 103 43 896

(51) Int. Cl.

| G01N 33/00 | (2006.01) |
|---|---|
| B01L 3/00 | (2006.01) |
| A61B 5/145 | (2006.01) |
| A61B 10/00 | (2006.01) |
| G01N 33/487 | (2006.01) |
| A61B 5/15 | (2006.01) |
| B01L 9/00 | (2006.01) |
| G01N 35/00 | (2006.01) |

(52) U.S. Cl.
CPC ........ *B01L 3/5023* (2013.01); *A61B 5/14532* (2013.01); *A61B 5/150022* (2013.01); *A61B 5/150358* (2013.01); *A61B 10/007* (2013.01); *A61B 10/0045* (2013.01); *G01N 33/48764* (2013.01); *A61B 2562/0295* (2013.01); *B01L 9/52* (2013.01); *B01L 2300/0812* (2013.01); *G01N 35/00009* (2013.01)

(58) Field of Classification Search
USPC .......................... 422/50, 55, 56, 57, 58, 100
See application file for complete search history.

(56) References Cited

U.S. PATENT DOCUMENTS 5,077,010 A * 12/1991 Ishizaka et al. ................ 422/56
5,228,972 A  7/1993 Osaka et al.

FOREIGN PATENT DOCUMENTS

| DE | 198 19 407 A1 | 11/1999 |
|---|---|---|
| DE | 198 49 539 | 5/2000 |
| EP | 0 299 517 | 1/1989 |
| WO | WO 02/100274 A1 | 12/2002 |

* cited by examiner

*Primary Examiner* — Sam P Siefke
(74) *Attorney, Agent, or Firm* — Bose McKinney & Evans LLP

(57) ABSTRACT

A test instrument for analyzing body fluids such as blood or urine. The instrument includes a wound test tape which can be transported from a storage space into a waste space by advancing the tap. The test tape has a plurality of test sections to which body fluid can be applied at a receiving position and also includes a measuring unit for detecting a constituent of the body fluid on an active test section. In order to carry out auxiliary instrument functions, in addition to the test sections, the test tape has one or more functional sections which can be brought into a functional position by advancing the tape.

4 Claims, 1 Drawing Sheet

TEST DEVICE FOR ANALYZING BODY FLUIDS

RELATED APPLICATIONS

This is a continuation application of International Application PCT/EP2004/010289 filed on Sep. 15, 2004, which claims priority to DE 103 43 896.3, filed on Sep. 19, 2003.

BACKGROUND

The present invention relates in general to a test device for analyzing body fluids such as blood or urine and in particular to a test tape which is preferably provided in a tape cassette such that the tape can be transported from a storage space into a waste space by advancing the tape.

Regular blood sugar monitoring is essential for diabetics because their treatment, diet and rhythm of life must often be adjusted based upon their monitored glucose levels. Handheld instruments that operate as "mini-laboratories" are widely available for self-monitoring and allow the necessary steps to be carried out simply and rapidly, even by laymen. Typically, disposable test strips are provided that are inserted into the instrument for determining glucose level, for example, by an optical measuring unit after the test strip is dosed with capillary blood. However, the storage and processing of these test strips requires a large amount of space and also requires complicated drives.

EP Applications No. 02026242.4 and 02028894.0 propose that a wound test tape on which a plurality of test sections provided with a suitable test chemistry are arranged consecutively should be used instead of individual test strips. The body fluid is applied and analyzed on a test section that is moved into an active position by advancing the tape. These patent applications give details about blood collection and also on the known test media and detection systems, especially for blood glucose, to which reference is herewith made and the content thereof is incorporated into this application.

SUMMARY OF THE INVENTION

The present invention addresses the disadvantages noted above and improves and simplifies an instrument of the aforementioned type in order to achieve a reliable measurement process.

In one form thereof, the present invention provides a test instrument for analyzing body fluids. The instrument includes a test tape that can be transported from a storage space to a waste space by advancing the tape, and the test tape has a plurality of test sections to which body fluid can be applied at a receiving position of the instrument. The test section comprises a reagent which reacts with the body fluid to produce a response to a constituent in the body fluid. A measuring unit is disposed in the test instrument for detecting the constituent of the body fluid on an active test section. The test tape also includes a functional section for performing an auxiliary instrument function. The functional section is moveable to a functional position by advancing the test tape.

The idea behind exemplary embodiments of the present invention is to obtain additional functionality from a tape transport that is already required to successively position the test sections. Accordingly, exemplary embodiments incorporating the present invention provide a test tape that has test sections and also has at least one functional section for an auxiliary instrument function that can be moved into a functional position by advancing the tape. In this manner, it is possible to utilize otherwise unused tape sections outside the test areas (e.g., between the test sections) to automatically bring about additional functions during tape advancement outside of the actual measurement.

According to an advantageous exemplary embodiment, the functional sections interact with the measuring unit in the functional position. However, it is also possible that the functional section is, for example, optically, electrically or magnetically scanned by a separate detection unit.

In order to improve the measuring accuracy, exemplary embodiments provide a functional section that has in particular a white, black, grey, coloured or transparent calibration field which is especially useful for the optical calibration of the measuring unit.

Another advantage is provided in other exemplary embodiments by a comparator that compares a measured value with a target value detected on an unused test section. Such a comparator can include a comparator circuit or software on an evaluation processor. Each functional section can comprise a calibration field for calibrating the measuring unit. Further, the test instrument may comprise a comparator configured to compare a measured value detected on an unused test section or functional section with a target value.

For automatic cleaning as the tape is advanced, it is advantageous to provide the functional section with a cleaning field which comes into contact with the measuring unit when the tape is advanced.

In other exemplary embodiments, a protective function can be achieved by providing a functional section that has a protective field designed to protect the measuring unit and in particular an elastically stretchable protective field.

It is also advantageous when the functional section includes a sensor or sensor field for detecting environmental parameters such as temperature or air humidity.

In order to control the measuring process of the measuring unit it is advantageous when the functional section includes a control field, which, in certain exemplary embodiments, comprises a metal foil.

The functional section can have an information field that can be read directly in plain text for user information. An advantageous embodiment provides that the information fields are arranged between the test sections and are numbered to indicate the number of remaining test sections that are still available, i.e., unused.

A further improvement of functionality and in particular of hygiene is achieved by a functional section that in certain embodiments includes an absorbent field designed for body fluid disposal. In this connection, it is also possible that the functional section can include a preservative that can be, for example, activated by moisture.

The functional section or sections are advantageously designed as a multifunctional field for a combination of several auxiliary instrument functions.

The test tape can be advantageously reeled off or unwound from a supply spool in the storage space, guided by a guide or guiding means in the area of the receiving position and reeled onto or wound into a take-up spool in the waste space.

In order to provide a suitable test chemistry it is advantageous when the test sections consist of a reagent coating that is applied in sections to a continuous carrier tape.

Another improvement especially in handling is achieved by the fact that the test tape in certain embodiments may be provided in a tape cassette that can be inserted into a housing of a portable instrument. A corresponding tape cassette as a consumable for use in a test instrument is also subject matter of the present invention.

BRIEF DESCRIPTION OF DRAWINGS

The above-mentioned aspects of the present invention and the manner of obtaining them will become more apparent and the invention itself will be better understood by reference to the following description of the embodiments of the invention taken in conjunction with the accompanying drawings, wherein.

Corresponding reference characters indicate corresponding parts throughout the several views.

DETAILED DESCRIPTION

The embodiments of the present invention described below are not intended to be exhaustive or to limit the invention to the precise forms disclosed in the following detailed description. Rather, the embodiments are chosen and described so that others skilled in the art may appreciate and understand the principles and practices of the present invention.

Figure 1:
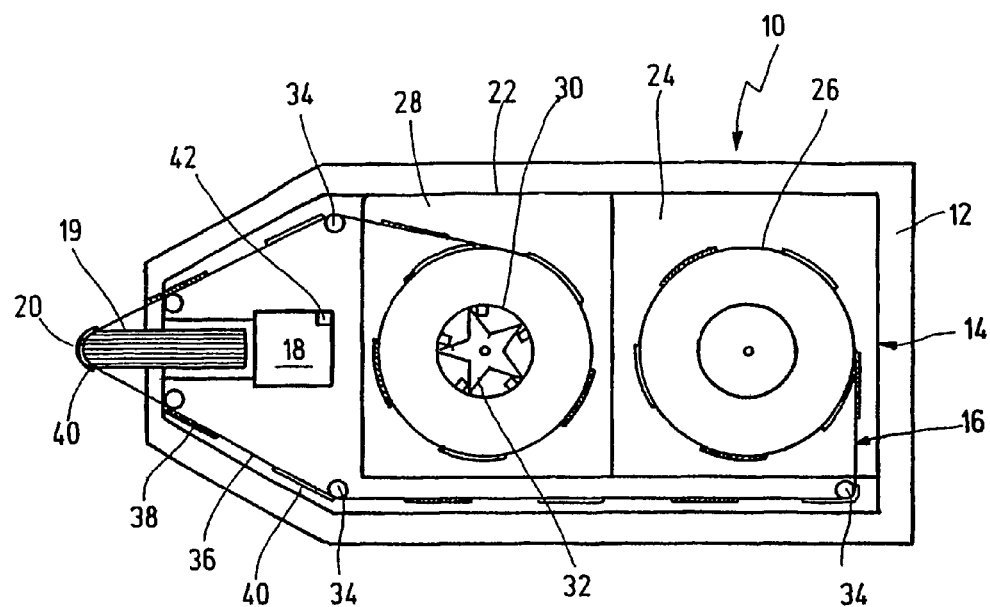
FIG. 1 shows a portable blood sugar measuring instrument for diabetics with a test tape in a simplified sectional view.

The blood sugar measuring instrument 10 shown in FIG. 1 comprises an instrument housing 12, a tape cassette 14 with a test tape 16 that is inserted therein and an optical measuring unit 18 for analyzing blood applied to the test tape. The measuring unit 18 is coupled with a guide tip 19 in the area of a blood receiving position 20 for the targeted application of a drop of blood on the test tape. The general principle of the instrument is described in detail in the EP Application No. 02026242.4 to which reference is made and the contents thereof are herewith incorporated.

The tape cassette 14 has a cassette housing 22 with a storage chamber 24 for a supply spool 26 and a storage chamber 28 for a take-up or waste spool 30. A spool drive 32 enables the test tape 16 to be advanced in sections from the storage spool 26 onto the take-up spool 30. The part of the test tape 16 that runs free between the spools 26, 30 is guided over deflection rollers 34 and over the guide tip 19.

Figure 2:
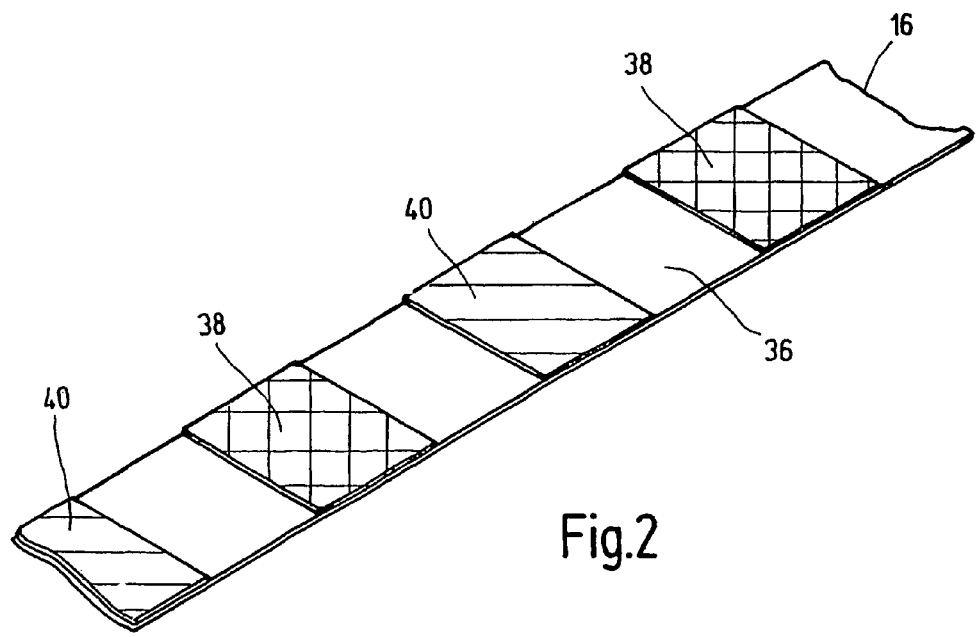
FIG. 2 shows the test tape with test sections and additional functional sections in a partial perspective view.

As can also be seen in FIG. 2, the test tape 16 has a continuous carrier foil 36 which is provided with test sections 38 for analytical purposes and additional functional sections 40 for the auxiliary instrument functions. The carrier foil 36 consists of a polymer foil of approximately 20 μm thickness which is, for example, made of polyester.

Reagent fields are applied in the area of the test sections 38 for example by gluing or labelling methods using prefabricated test elements or by means of direct coating methods and in particular printing methods. The reagent fields contain dry chemicals which respond with a color change to the analyte (glucose) in the applied blood fluid. This reaction is detected by a reflection-photometric measurement carried out by the measuring unit 18. In this connection, the measuring unit 18 is optically coupled via the guide tip 19 designed as a light guide and through the transparent carrier foil 36 to a section of test tape 38 which is at that moment active and located in the receiving position 20. The test sections 38 can be successively brought into use by an appropriate tape advance. In this manner it is possible to automatically carry out a plurality of tests for patient self monitoring without having to replace consumables.

During the tape transport the functional sections 40 also reach their respective functional position. In this connection an interaction with the measuring unit 18 may be provided as shown in FIG. 1. The functional sections 38 may alternatively or additionally have additional functions with regard to other instrument components or the user.

In the embodiment shown, the functional sections 40 are alternately applied with the test sections in the direction of tape movement (in the lengthwise direction of the test tape) and are applied to the carrier foil 36 on the same side of the tape as the tape sections by printing or gluing or by other suitable measures. Other arrangements are also conceivable, depending on the respective function, such as only at the start of the test tape 16 or on the rear side of the tape facing away from the blood application side.

In order to calibrate the optical measuring unit 18, the functional sections 38 can be formed by a calibration field with defined optical properties. White, black, grey or coloured fields can be used for this purpose. The calibration can compensate for aging or other change between the time the tape was manufactured and the time of use to thus ensure accuracy of measurement. Colored fields can be used for wavelength control or for drift correction, for example, in the case of temperature variations. An area of the transparent carrier foil 36 which reflects almost no light may already be sufficient for the dark calibration. The target values of the calibration fields are expediently fed into the instrument 10 in a batch-specific manner, e.g., by means of a functional field 40 as a coding or storage medium which interacts with an evaluation unit that is not shown.

The measuring unit 18 is calibrated by means of a comparator 42 by comparison with a target value or characteristic field that is deposited in the instrument. The adjustment of the measuring unit 18 also enables a very accurate control of the blank value on an unused test section 38. This allows a very sensitive detection of a discoloration or other change that indicates unusability.

A cleaning function can be achieved by applying a functional field 40 made of a soft material such as felt or paper on the rear side of the carrier tape 36 facing the measuring unit 18. When the tape is advanced, this cleaning field glides over the measuring window and thus automatically removes dirt and dust without requiring additional instrument or user interventions.

In the resting state the optical system of the measuring unit 18 is hardly protected by the thin transparent carrier tape 36. As a remedy, a functional section 40 that is suitable as a protective field can be located in front of the optical system in the resting position in order to improve screening against environmental influences. An elastic flat piece of material is, for example, suitable for this. Such a protective field can also be guided more reliably, thus preventing it from sliding off sideways from the guide tip 19.

Another application of the functional sections 40 is for fields that change color in a temperature-dependent manner to act as sensors for the current temperature or the temperature during storage and optionally indicate that a temperature has been exceeded. A moisture-sensitive functional field could also be provided to warn against unsuitable conditions.

A metal foil as a functional section 40 on the carrier tape 36 and an approximation switch in the instrument 10 could trigger start and stop signals or control an instrument flap. Metal foils of different resistances can be read electrically. A magnetizable piece of foil could be read and also written.

In addition, the functional sections may contain information that can be directly read by the user, such as an alpha or numeric character that indicates the number of test sections 38 that are still available, i.e., unused. This would allow the user to read the number of remaining stock even on a cassette 14 removed from the instrument 10. A colored, e.g. red, warning field positioned before the last few test sections 38 on the tape could make the user aware that the tape will be depleted soon.

Another additional function is for an absorbent functional field 40 to take up an excess of blood sample so that it can dry hygienically in the waste chamber 28. A functional field containing a preservative could if required further improve the hygiene in the waste chamber 28.

The functional field 40 may also simultaneously provide several auxiliary functions. For example, a somewhat thicker white paper field can be used for calibration, cleaning and protection. The beginning of this field cleans after the measurement. The middle part is in front of the lens system during the period of non-use and protects it. The current test number is printed visibly for the user on the middle part. The end part is used before the new measurement to calibrate the optical system. Excess blood is taken up in the waste chamber 28 which improves the hygiene.

Having described several advantageous embodiments above, one of skill in the art can now readily appreciate that exemplary embodiments of the present invention provide a test tape that not only includes test sections which are typically used to detect or determine concentration of a constituent in a body fluid, but also provides functional sections that can perform one or more of a variety of auxiliary functions.

While exemplary embodiments incorporating the principles of the present invention have been disclosed hereinabove, the present invention is not limited to the disclosed embodiments. Instead, this application is intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A test instrument for analyzing body fluids, comprising:
a test tape that can be transported from a storage space to a waste space by advancing the tape, the test tape having a plurality of test sections to which body fluid can be applied at a receiving position, the test sections comprising a reagent which reacts with the body fluid to produce a response to a constituent in the body fluid;
a measuring unit for detecting the constituent of the body fluid on an active one of the test sections, wherein the measuring unit comprises an optical measuring unit;
the test tape comprising a functional section for an auxiliary instrument function, the functional section being moveable to a functional position by advancing the test tape, wherein the functional section includes a calibration field for calibrating the measuring unit, the calibration field including a white, black, grey, colored or transparent calibration field; and
wherein the measuring unit further comprises a comparator configured to compare a measured value detected on the calibration field with a target value resident in the instrument.

2. The test instrument of claim 1 wherein the functional section comprises a plurality of functional sections comprising a calibration field, the test sections and functional sections comprising a calibration field alternating along the lengthwise direction of the tape.

3. A test instrument for analyzing body fluids, comprising:
a test tape that can be transported from a storage space to a waste space by advancing the tape, the test tape having a plurality of test sections to which body fluid can be applied at a receiving position, the test sections comprising a reagent which reacts with the body fluid to produce a response to a constituent in the body fluid;
a measuring unit for detecting the constituent of the body fluid on an active one of the test sections, wherein the measuring unit comprises an optical measuring unit;
the test tape comprising a functional section for an auxiliary instrument function, the functional section being moveable to a functional position by advancing the test tape, wherein the functional section includes a calibration field for calibrating the measuring unit, the calibration field including a white, black, grey, colored or transparent calibration field; and
wherein the measuring unit further comprises a comparator configured to compare a value measured on the calibration field with a target value.

4. The test instrument of claim 3, wherein the functional section comprises a plurality of functional sections and the test sections and functional sections alternate along the lengthwise direction of the test tape.

\* \* \* \* \*